United States Patent

Kimura et al.

[11] Patent Number: 5,820,696
[45] Date of Patent: Oct. 13, 1998

[54] METHOD OF CLEANING AND DISINFECTING CONTACT LENS

[75] Inventors: Norio Kimura, Kasugai; Akira Nakagawa, Yokkaichi; Hiroyasu Satoh, Anjo, all of Japan

[73] Assignee: Tomey Technology Corporation, Japan

[21] Appl. No.: 690,541

[22] Filed: Jul. 31, 1996

[30] Foreign Application Priority Data

Aug. 2, 1995 [JP] Japan ................................. 7-197589

[51] Int. Cl.⁶ .............................. C11D 3/386; B08B 3/04
[52] U.S. Cl. ...................... 134/42; 510/112; 510/113; 510/114; 510/115; 510/392; 510/530; 435/263; 435/264; 422/28; 134/42
[58] Field of Search ................................ 510/112, 113, 510/114, 115, 392, 530; 435/263, 264; 422/28; 134/42

[56] References Cited

U.S. PATENT DOCUMENTS

| | | | |
|---|---|---|---|
| 4,670,178 | 6/1987 | Huth et al. | 252/95 |
| 4,812,173 | 3/1989 | Tsao | 134/27 |
| 5,096,607 | 3/1992 | Mowrey-McKee et al. | 252/106 |
| 5,281,277 | 1/1994 | Nakagawa et al. | 134/18 |
| 5,314,823 | 5/1994 | Nakagawa et al. | 435/264 |
| 5,356,555 | 10/1994 | Huth et al. | 252/106 |
| 5,422,073 | 6/1995 | Mowrey-McKee | 422/28 |
| 5,460,658 | 10/1995 | Nakagawa et al. | 134/42 |
| 5,532,224 | 7/1996 | Desai et al. | 514/63 |
| 5,576,278 | 11/1996 | Van Duzee et al. | 510/114 |
| 5,604,190 | 2/1997 | Chowhan et al. | 510/114 |
| 5,672,213 | 9/1997 | Asgharian et al. | 134/42 |

FOREIGN PATENT DOCUMENTS

| | | |
|---|---|---|
| 0 456 467 A2 | 11/1991 | European Pat. Off. . |
| 0 462 460 A2 | 12/1991 | European Pat. Off. . |
| 50-126245 | 10/1975 | Japan . |
| 2-168224 | 6/1990 | Japan . |
| 9625957 | 8/1996 | Japan . |

*Primary Examiner*—Paul Lieberman
*Assistant Examiner*—Kery A. Fries
*Attorney, Agent, or Firm*—Parkhurst & Wendell, L.L.P

[57] ABSTRACT

A method of simultaneously cleaning and disinfecting a contact lens is disclosed, which method comprises the steps of: (a) preparing a cleaning solution for the contact lens comprising an effective amount of a proteolytic enzyme, 15–60 w/v % (percent by weight/volume) of propylene glycol, 10–60 w/v % of glycerine, and water, a total content of the propylene glycol and glycerine being in a range of 30–80 w/v %; (b) diluting the cleaning solution with a disinfecting or storing liquid for the contact lens which contains an ionic antimicrobial agent, so as to provide a dilution; and (c) immersing the contact lens in the dilution.

18 Claims, No Drawings

METHOD OF CLEANING AND DISINFECTING CONTACT LENS

BACKGROUND OF THE INVENTION

1. Field of the Invention

The present invention relates to a method of cleaning and disinfecting a contact lens, and more particularly to such a method which assures simple and efficient cleaning and disinfection of the contact lens by effecting cleaning and disinfection of the contact lens at the same time in a single step.

2. Discussion of the Related Art

Generally, a contact lens is classified into a non-water contained contact lens and a hydrogel contact lens, or into a hard contact lens and a soft contact lens. These contact lenses are likely to be soiled with stains such as protein and lipid included in the tear fluid during wearing of the contact lenses on the eyes of the user. These stains adhering to the contact lenses undesirably deteriorate the wearing comfort of the contact lenses as felt by the user, lower the eyesight of the user, and cause various troubles to the eyes such as hyperemia of the conjunctiva. In view of this, it is required to regularly clean the contact lenses to remove the stains therefrom for comfortable and proper wearing of the contact lenses on the user's eyes.

In a conventional method of cleaning the contact lens for removal of the stains adhering to the contact lens, for example, the lipid stain is removed from the contact lens by rubbing the lens with a cleaning solution which includes a surface active agent, while the protein stain is removed by immersing the contact lens in a cleaning solution which includes a proteolytic enzyme.

For removing the protein stain from the contact lens, a solid cleaning agent in tablet or granular form is conventionally used. More specifically described, such a solid cleaning agent is dissolved in an exclusive storing or preserving liquid or physiological salt solution, and the contact lens soiled with the protein stain is immersed in the solution for a predetermined time to remove the protein stain from the contact lens. However, this method undesirably requires a cumbersome procedure of dissolving the cleaning agent.

In view of a fact that the proteolytic enzyme is generally unstable in a dilute solution, and in order to avoid the above-described cumbersome procedure of dissolving the solid cleaning agent, there is proposed a liquid-type cleaning agent in which the proteolytic enzyme is stabilized in the form of a solution. Such a liquid-type cleaning agent is commercially available. For instance, JP-A-2-168224 discloses a method of cleaning the contact lens using a contact lens cleaning liquid which consists of the proteolytic enzyme, an organic liquid which is miscible with water, and water. More specifically described, the cleaning liquid is diluted with an aqueous medium so as to provide a dilution or dilute solution. The contact lens is immersed in the thus prepared dilution to remove the protein stain adhering to the contact lens. However, this Publication discloses only the method of cleaning the contact lens, and never teaches a use of the cleaning liquid in combination with a disinfecting liquid, and a method of disinfecting the contact lens. When the cleaning liquid is diluted with the disinfecting liquid used for the contact lens, the disinfecting effect to be exhibited by the disinfecting liquid may be lowered by some components included in the cleaning liquid.

In general, bacteria or germs tend to adhere to, and proliferate on, the surfaces of the contact lens, especially the surfaces of the hydrogel contact lens. In view of this, it is necessary to disinfect the contact lens every day for the purpose of preventing the eyes of the lens user from being infected with the bacteria or germs. Even the non-water contained contact lens should be necessary to be applied a suitable antimicrobial agent for preventing proliferation of the bacteria while the lens is stored in the storing liquid.

For disinfecting the contact lens, there are conventionally known a heat disinfecting method in which the contact lens is heated, and a chemical disinfecting method which utilizes a chemical disinfectant. In the heat disinfecting method, the contact lens which is immersed in a saline or in a saline that contains the antimicrobial agent is heated at a temperature higher than 80° C., so that the contact lens is disinfected. In the chemical disinfecting method, the contact lens is immersed in a disinfecting or storing liquid which contains the antimicrobial agent. Examples of the antibacterial agent used in the chemical disinfecting methods include an oxidizing agent such as hydrogen peroxide, an anionic chemical substance such as sorbic acid or benzoic acid, and a cationic chemical substance such as chlorhexidine, polyhexamethylene biguanide, $\alpha$-4-[1-tris(2-hydroxyethyl)ammonium-2-butenyl]poly[1-dimethylammonium-2-butenyl]-$\omega$-tris(2-hydroxyethyl)ammonium chloride.

The above-described heat disinfecting method is inconvenient since it requires a device equipped with an electric source for heating the contact lens. When the oxidizing agent such as hydrogen peroxide is used as the antimicrobial agent, it requires an additional step of decomposing peroxide after the contact lens is disinfected since the peroxide is very harmful to the eye. The cationic chemical substance exhibits a relatively high degree of antimicrobial activity and is not harmful to the eye as compared with the peroxide. Thus, the cationic chemical substance is widely used as the antimicrobial agent in various countries. The anionic chemical substance exhibits relatively mild antimicrobial activity as compared with the cationic chemical substance, and is employed in the storing liquid for the non-water contained contact lens, solvent for dissolving the proteolytic enzyme, and soaking liquid which is used in the above-described heat disinfecting method.

Generally, the contact lens is cleaned and disinfected in different steps. However, it would be more convenient to the contact lens user if the contact lens is cleaned and disinfected simultaneously in a single step. Thus, there are proposed various methods of simultaneously cleaning and disinfecting the contact lens.

For instance, U.S. Pat. No. 4,670,178 (JP-A-62-59918) discloses a method of simultaneously effecting of the cleaning of the contact lens for removal of the protein stain and the sterilizing of the contact lens, wherein the contact lens is kept in contact with a solution for a sufficient period, which solution contains a peroxide-active proteolytic enzyme and peroxide such as hydrogen peroxide. However, in this method, the peroxide must be decomposed after the contact lens is cleaned and disinfected since the peroxide is considerably harmful to the eye. Further, the proteolytic enzyme used in the disclosed method is provided in the form of solid such as a tablet.

JP-A-50-126245 discloses a method of cleaning and disinfecting the contact lens, in which the contact lens is held in contact with a mixture consisting of: quaternary ammonium salt having a specific structure such as alkyl(tallow) triethanolamine ammonium chloride; non-toxic polymer such as water-soluble polyhydroxymethyl methacrylate; and proteolytic enzyme. In this method, too, the proteolytic enzyme is provided in the form of solid such as a tablet.

U.S. Pat. No. 5,096,607 (JP-A-2-289255) discloses a method of simultaneously cleaning and sterilizing the contact lens, by immersing the contact lens in a treatment liquid which comprises the proteolytic enzyme and antimicrobial agent and whose osmotic pressure is held at a level adjacent to a physiological state. This method was developed in view of a fact that the sterilizing effect to be exhibited by the antimicrobial agent is not likely to be inhibited when the treatment liquid has the osmotic pressure value adjacent to the physiological state. This publication, however, does not indicate the form of the proteolytic enzyme to be used in the treatment liquid.

EP-A-0456467 (JP-A-4-231054) discloses a two-part composition which consists of a first component and a second component, and a method of cleaning and disinfecting the contact lens using the two-part composition. Described more specifically, the first component consists of a nitrogen-containing polymeric antimicrobial agent such as a polymeric quaternary ammonium compound and a complexing agent which is selected from a group consisting of citric acid, ethylenediaminetetraacetic acid, acetic acid and salts of these acids, while the second component is an enzyme. The first and second components are included in the composition at a predetermined ratio. In this method, too, the proteolytic enzyme is provided in solid form such as a tablet.

In simultaneously cleaning and disinfecting the contact lens by using the proteolytic enzyme as described above, it may be considered that the proteolytic enzyme is provided in solution form to eliminate the cumbersome procedure of dissolving the solid proteolytic enzyme. In this case, the proteolytic enzyme in solution form is diluted with a sterilizing or storing liquid which contains the above-described anionic or cationic chemical substance. However, this method undesirably suffers from some problems as indicated below.

The conventionally used cleaning liquid or solution containing the proteolytic enzyme needs to be added the anionic or cationic chemical substance as an antiseptic agent for the purpose of preventing the proliferation of the microorganisms during storage of the contact lens. When the cleaning liquid containing the anionic chemical substance is diluted with the disinfecting or storing liquid containing the cationic chemical substance, the antimicrobial activity of the disinfecting or storing liquid is undesirably lowered. On the other hand, when the cleaning liquid contains the cationic chemical substance, the antimicrobial activity of the storing liquid which contains the anionic chemical substance is lowered. Thus, different cleaning liquids need to be prepared depending upon the kinds of the disinfecting or storing liquid which contains the anionic or cationic chemical substance. In other words, a specific cleaning liquid must be used in combination with a specific disinfecting or storing liquid. When the cleaning liquid is erroneously used with an improper disinfecting or storing liquid, the microorganisms might be proliferated.

For improving the cleaning effect of the cleaning liquid with respect to the lipid stain, a surface active agent may be added to the cleaning liquid. However, it is revealed that such a surface active agent sometimes lowers the antimicrobial activity of the disinfecting or storing liquid with which the cleaning solution is diluted.

SUMMARY OF THE INVENTION

The present invention was developed in the light of the above-described situation. It is therefore an object of the invention to provide a method of simultaneously effecting the cleaning of a contact lens for removal of the stain adhering to the lens, especially, protein stain, and the disinfection of the contact lens, by applying a cleaning solution which contains a proteolytic enzyme to a contact lens disinfecting or storing liquid which contains an ionic antimicrobial agent, while assuring simplified and safe handling of the contact lens.

It is an optional object of the invention to provide a method of cleaning and disinfecting the contact lens wherein the cleaning solution including the proteolytic enzyme advantageously exhibits a sufficient preservative effect so as to inhibit proliferation of the microorganisms while the cleaning solution does not substantially lower the antimicrobial activity of the contact lens disinfecting or storing liquid when the cleaning solution is diluted with the disinfecting or storing liquid that contains one of cationic or anionic antimicrobial agents.

As a result of an extensive research made by the present inventors, there is found a cleaning solution for a contact lens in which the proteolytic enzyme is stable in the presence of predetermined amounts of propylene glycol and glycerine while exhibiting a sufficient degree of the preservative effect. This contact lens cleaning solution does not deteriorate the antimicrobial activity of various contact lens disinfecting agents or storing liquids that contain different kinds of ionic antimicrobial agents when the cleaning solution is diluted with the disinfecting or storing liquids. Further, the inventors found a method of simultaneously cleaning and disinfecting the contact lens by using such a contact lens cleaning solution.

The above-indicated objects of the invention may be attained according to a principle of the present invention which provides a method of simultaneously cleaning and disinfecting a contact lens comprising the steps of: (a) preparing a cleaning solution for the contact lens comprising an effective amount of a proteolytic enzyme, 15–60 w/v % (percent by weight/volume) of propylene glycol, 10–60 w/v % of glycerine, and water, a total content of the propylene glycol and the glycerine being in a range of 30–80 w/v %; (b) diluting the cleaning solution with a disinfecting or storing liquid for the contact lens which contains an ionic antimicrobial agent, so as to provide a dilution or dilute solution; and (c) immersing the contact lens in the dilution.

The cleaning solution employed in the present method of cleaning and disinfecting the contact lens contains 15–60 w/v % of propylene glycol and 10–60 w/v % of glycerine, and the total content of the propylene glycol and glycerine is held in a range of 30–80 w/v %, so that the effective amount of proteolytic enzyme is effectively stabilized in the cleaning solution while the cleaning solution assures sufficient preservative effect. Further, the cleaning solution prepared as described above does not deteriorate the antimicrobial effect of the contact lens disinfecting liquids that contain different kinds of the ionic antimicrobial agents when the cleaning solution is applied to the disinfecting liquids. According to the present invention, the contact lens is simultaneously cleaned and disinfected in a simplified manner with high efficiency.

According to one preferred form of the invention, the cleaning solution further comprises a nonionic surface active agent in an amount up to 10 w/v %. The nonionic surface active agent is effective to improve the cleaning effect of the cleaning solution with respect to the lipid stain, and is preferably employed in the present invention since the nonionic surface active agent does not adversely influence the effect of stabilizing the proteolytic enzyme exhibited by the predetermined amounts of the propylene glycol and glycerine, and the preservative effect of the cleaning solution. Further, the nonionic surface active agent does not deteriorate the antimicrobial activity of the disinfecting or storing liquid when the cleaning solution is applied to the disinfecting or storing liquid that contains the ionic antimicrobial agent.

According to another preferred form of the invention, the proteolytic enzyme included in the cleaning solution is serine protease, and the cleaning solution further comprises calcium ions in a concentration of 0.5–250 mM/l. The serine protease is stabilized in the presence of the calcium ion, so that the cleaning solution is capable of exhibiting enhanced cleaning ability with respect to the protein stain.

According to still another preferred form of the invention, the ionic antimicrobial agent which is included in the disinfecting or storing liquid used for diluting the cleaning solution is selected from the group consisting of biguanides, quaternary ammonium salts, sorbic acid, benzoic acid and salts thereof.

DETAILED DESCRIPTION OF THE PREFERRED EMBODIMENT

The proteolytic enzyme is included in the cleaning solution so as to remove the protein stain adhering to the contact lens. The amount of the proteolytic enzyme included in the cleaning solution is suitably determined depending upon the cleaning effect or detergency to be exhibited by the proteolytic enzyme. In general, the effective amount of the proteolytic enzyme included in the cleaning solution is in a range of 0.1–10 w/v %, preferably, 0.5–5 w/v %. The proteolytic enzyme is generally classified, depending on kinds of a residue in an active site thereof, into: serine protease; thiol protease; metal protease; and carboxyl protease. In particular, the serine protease is favorably used as the proteolytic enzyme included in the contact lens cleaning solution according to the present invention. This is because the serine protease does not need any cofactor for activation of the enzyme, to thereby assure easy handling thereof. On the other hand, the thiol protease needs to be activated, making the handling cumbersome.

Described more specifically, when the serine protease is included as the proteolytic enzyme in the cleaning solution, it exhibits a sufficient enzyme activity in a neutral range without requiring the cofactor such as a reducing agent. Further, the enzyme activity of the serine protease is not rapidly deactivated even in the presence of a metal chelate agent. On the other hand, when the thiol protease is used as the proteolytic enzyme in the cleaning solution, it requires the reducing agent as the cofactor.

However, since such a reducing agent is considerably unstable in an aqueous solution, the thiol protease does not exhibit its effect to a satisfactory extent. When the carboxyl protease is used as the proteolytic enzyme, it is necessary to keep the cleaning solution acidic for permitting the carboxyl protease to exhibit a sufficient degree of the enzyme activity. However, in view of a fact that the contact lens cleaning solution may contact with fingers and eyes of the contact lens user, it is not desirable to keep the cleaning solution acidic since such an acidic cleaning solution may cause a high degree of irritation to the living body. The metal protease has a metal ion in its active site. Since the disinfecting or storing liquid which is used for diluting the cleaning solution and which includes the ionic antimicrobial agent often contains the metal chelating agent, the enzyme activity exhibited by the metal protease may be rapidly deactivated during the process of cleaning and disinfecting the contact lens.

The serine protease preferably used as the proteolytic enzyme in the present invention has a serine residue in its active site. Examples of the serine protease include trypsin, chymotrypsin derived from the animal, and protease derived from the bacteria, antinomycetes and mold. Various kinds of the protease derived from Bacillus are commercially available, such as "BIOPRASE" from NAGASE SEIKAGAKU KOGYO K. K., Japan, "Clear Lens Pro" from Novo Nordisk Bioindustry Ltd., Denmark, "Alkaline Protease GL-440" from Kyowa-Solzyme K. K., Japan.

The serine protease derived from Bacillus has portions in the molecule adapted to bond with calcium ion. With the calcium ion being bonded to the portions as described above, the enzyme has a stable molecular structure. When the serine protease derived from Bacillus is used as the proteolytic enzyme in the present contact lens cleaning solution, the calcium ion is added to the cleaning solution so as to increase the stability of the proteolytic enzyme. Accordingly, the contact lens cleaning solution used in the present invention effectively assures improved detergency with respect to the protein stain.

The calcium ion is generally provided in the form of a calcium salt which has good water solubility, such as calcium chloride, calcium sulfate or calcium acetate. The calcium salt is added as the calcium ion to the cleaning solution in a concentration of 0.5–250 mM/l, preferably, 3–30 mM/l. If the concentration of the calcium ion is lower than 0.5 mM/l, the calcium ion does not exhibit sufficient effect of stabilizing the enzyme. On the other hand, the enzyme stabilizing effect exhibited by the calcium ion does not significantly increase if the concentration of the calcium ion increases above the upper limit of 250 mM/l.

When the proteolytic enzyme is provided in solution form, a suitable organic solvent is added thereto in view of a fact that the proteolytic enzyme is unstable in the aqueous solution. It is necessary to select the organic solvent which assures a high degree of safety with respect to the living body without adversely influencing the material of the contact lens. In view of this, the glycerine and propylene glycol are employed as the organic solvent in the present invention. That is, the present contact lens cleaning solution employs a mixed solvent wherein the glycerine and propylene glycol are mixed in water in the respective proportions. The glycerine and propylene glycol function to stabilize the proteolytic enzyme so that the proteolytic enzyme is stable in the solution, to thereby assure improved cleaning effect of the cleaning solution with respect to the protein stain. In particular, the glycerine is effective to stabilize the enzyme in the aqueous solution without adversely influencing the sterilizing effect of the disinfecting or storing liquids when the cleaning solution is diluted with the disinfecting or storing liquid that contain different kinds of ionic antimicrobial agent.

The propylene glycol does not only stabilize the proteolytic enzyme, but also exhibits excellent sterilizing or disinfecting effect and cleaning effect for removal of the lipid stain. Thus, the cleaning solution prepared according to the present invention is capable of exhibiting excellent lipid-stain removal effect and disinfecting effect, in addition to the cleaning effect exhibited by the proteolytic enzyme. Accordingly, the present cleaning solution including the propylene glycol functions to prevent proliferation of the microorganisms even if the cleaning solution does not include other components which are generally used for sterilizing. If such sterilizing components are included in the cleaning solution, those components may interact with the proteolytic enzyme, resulting in considerable reduction in the cleaning ability or detergency and sterilizing effect of the cleaning solution. Further, the sterilizing components may adversely influence the sterilizing effect when the cleaning solution is diluted with various disinfecting or storing liquids which contain different kinds of ionic antimicrobial agent. However, the present cleaning solution does not suffer from such problems since the cleaning solution including the propylene glycol does not require such sterilizing components.

For advantageously obtaining the excellent effects of the propylene glycol as described above, the propylene glycol is included in the cleaning solution in an amount of 15–60 w/v %, preferably 20–40 w/v %. The cleaning solution does not exhibit satisfactory effect of preventing proliferation of the microorganisms when the amount of the propylene glycol is below 15 w/v %. The effect of preventing proliferation of the microorganisms exhibited by the propylene glycol does not increase with an increase in the amount of glycerine above the upper limit of 60 w/v %. Further, the inclusion of the propylene glycol in an amount exceeding the upper limit may even cause a rise in the osmotic pressure when the cleaning solution is diluted with the contact lens disinfecting or storing liquid.

The glycerine is included in the cleaning solution in an amount of 10–60 w/v %, preferably 20–40 w/v %. If the amount of the glycerine is smaller than 10 w/v %, the enzyme needs to be stabilized by the propylene glycol alone, leading to insufficient stabilization of the enzyme. The enzyme stabilizing effect exhibited by glycerine does not increase with an increase in the amount of the glyccerine above the upper limit of 60 w/v %. Further, the inclusion of the glycerine in an amount exceeding the upper limit may even cause a rise in the osmotic pressure and a deterioration of the solubility of the other components.

The total content of the propylene glycol and glycerine is generally in a range of 30–80 w/v %, preferably 40–60 w/v %. If the total content is below 30 w/v %, the proteolytic enzyme is not sufficiently stabilized. The enzyme stabilizing effect does not increase with an increased in the total content of the propylene glycol and glycerine above the upper limit of 80 w/v %. The total content of the propylene glycol and glycerine exceeding the upper limit may even cause a deterioration in the solubility of the other components.

The cleaning solution employed in the present method of cleaning and disinfecting the contact lens advantageously contains a predetermined suitable surface active agent, for improving the cleaning effect with respect to the lipid stain included in the tear fluid and adhering to the contact lens, and for increasing the viscosity of the solution. It is necessary to select the surface active agent which assures a high degree of safety with respect to the living body without adversely influencing the contact lens material and deteriorating the stability of the proteolytic enzyme, and which does not cause an adverse influence when the cleaning solution is diluted with the disinfecting liquids that contain different kinds of the ionic antimicrobial agent. In view of this, the nonionic surface active agent is preferably used in the present invention for the following reasons. That is, the anionic surface active agent considerably lowers the sterilizing effect to be exhibited by the cationic sterilizing agent which is favorably used in the disinfecting liquid. The cationic and amphoteric surface active agents tend to adhere to the material of the hydrogel contact lens or cooperate with the anionic surface active agent included in the storing liquid for the non-water contained contact lens, so as to produce insoluble complex.

The nonionic surface active agent is included in the cleaning solution in an amount up to 10 w/v %, preferably in an amount of 0.1–3 w/v %. Examples of the nonionic surface active agent are polyoxyethylene-polyoxypropylene block copolymer, condensation product of polyoxyethylene and ethylenediamine, fatty acid glyceryl ester, alkanoic acid sucrose ester, polyoxyethylene alkylamine, sorbitan fatty acid polyoxyethylene ester, fatty acid triethanolamine ester, polyoxyethylene alkyl ether, polyoxyethylene alkylphenyl ether and polyoxyethylene polystyrylphenyl ether. In particular, the polyoxyethylene-polyoxypropylene block copolymer is preferably used in the present invention for assuring a high degree of safety.

The contact lens cleaning solution used in the present method of cleaning and disinfecting the contact lens comprises the four components consisting of the effective amount of the proteolytic enzyme, the respective amounts of the propylene glycol and glycerine, and water. Alternatively, the cleaning solution comprises the five components consisting of the effective amount of the proteolytic enzyme, the respective amounts of the propylene glycol and glycerine, water and nonionic surface active agent. In either case, the total content of these components included in the cleaning solution is 100 w/v %. To the cleaning solution prepared according to the present invention, the calcium ion may be added to increase the stability of the serine protease as described above. Similarly, a suitable buffer may be added to the cleaning solution for assuring the pH stability of the cleaning solution as discussed below.

The contact lens cleaning solution used in the present invention has a pH value which is held in a range of 5.0–9.5, preferably 5.5–7.5. If the pH value of the cleaning solution is lower than 5.0, the stability of the proteolytic enzyme is deteriorated, leading to insufficient cleaning effect. On the other hand, if the pH value is higher than 9.5, it would cause harm to the hands of the user, and give an adverse influence on the material of the contact lens.

For keeping the pH value of the cleaning solution in the range of 5.0–9.5, a suitable buffer is added to the cleaning solution. The buffer is suitably selected from among various known buffers which do not deteriorate the stability of the proteolytic enzyme. When the serine protease is included in the cleaning solution as the proteolytic enzyme and the calcium ion is added to the solution for stabilizing the serine protease, a suitable buffer is selected which does not cause precipitation in the cleaning solution due to interaction of the calcium ion and the buffer. Examples of such buffer include a buffer comprising tris(hydroxymethyl) aminomethane and hydrochloric acid, and a buffer comprising boric acid and/or borax. In the present invention, the buffer comprising boric acid and/or borax is preferably employed. The buffer is included in the cleaning solution generally in an amount of 0.1–10 w/v %. If the amount of the buffer is smaller than 0.1 w/v %, the pH stability of the cleaning solution is deteriorated. The pH stability does not increase with an increase in the amount of the buffer above the upper limit of 10 w/v %.

In simultaneously cleaning and disinfecting the contact lens by using the contact lens cleaning solution as described above, the cleaning solution is diluted with the contact lens disinfecting or storing liquid which contains the ionic antimicrobial agent. Examples of this ionic antimicrobial agent are anionic chemical substance such as sorbic acid or benzoic acid and salts thereof, biguanides such as polyhexamethylene biguanide or chlorhexidine, quaternary ammonium salts such as benzalkonium halide, or α-4-[1-tris(2-hydroxyethyl)ammonium-2-butenyl]poly[1-dimethylammonium-2-butenyl]-ω-tris(2-hydroxyethyl) ammonium chloride and derivatives thereof.

The contact lens disinfecting or storing liquid which contains the ionic antimicrobial agent is commercially available. Examples of the contact lens disinfecting liquid are "ReNu Multi-Purpose Solution" available from BAUSCH & LOMB INCORPORATED, U.S.A., "OPTI-FREE" (available from Alcon Laboratories Incorporated, U.S.A., "COMPLETE" (available from Allergan, Inc., U.S.A., and "SOLO CARE Soft" (available from CIVA VISION, U.S.A.). Examples of the contact lens storing liquid are "Sensitive Eyes Saline Solution for Soft Lenses" (available from BAUSCH & LOMB INCORPORATED, U.S.A.), and "Total" (available from Allergan, Inc., U.S.A.).

The contact lens is cleaned and disinfected in the following manner. Initially, several droplets of the contact lens cleaning solution according to the present invention are added to the above-described contact lens disinfecting or storing liquid, e.g., the commercially available disinfecting or storing liquid. The contact lens which was removed from the eye is soaked in the thus diluted cleaning solution for a predetermined time for disinfecting or storing the contact lens. The cleaning solution is suitably diluted with the disinfecting or storing liquid to achieve the desired cleaning and disinfecting effect. For cleaning and disinfecting the soft contact lens, it is desirable that the dilution obtained by diluting the cleaning solution with the disinfecting or storing liquid have a pH value in a range of 6.0–8.0, preferably 6.5–7.5 and an osmotic pressure value in a range of 200–600 mOsm, preferably 300–450 mOsm. The period during which the contact lens is soaked in the dilution is determined according to disinfecting time specified in the individual disinfecting liquids. In general, the contact lens is cleaned and disinfected to a sufficient extent by immersing the contact lens in the dilution for more than two hours. In case that the present cleaning solution is diluted with the commercially available storing liquid for the soft contact lens, the sufficient cleaning and disinfecting effect can also be obtained when the contact lens is subjected to the heat disinfecting method as described above.

The contact lens is cleaned for removal of the lipid and protein stains adhering to the contact lens and disinfected, simultaneously in a simplified manner, by a series of procedure according to the present invention, to thereby eliminate the conventionally required cumbersome procedure. The contact can be worn on the eye of the user by simply rinsing the contact lens after the cleaning and disinfecting treatment.

EXAMPLES

To further clarify the concept of the present invention, some examples of the invention will be described. It is to be understood that the invention is not limited to the details of the illustrated examples, but may be embodied with various changes, modifications and improvements, which may occur to those skilled in the art without departing from the scope of the invention defined in the attached claims.

Example 1

A specimen No. 1 of the cleaning solution for the contact lens according to the present invention was prepared in the following manner, so that the specimen No. 1 has the composition as indicated in TABLE 1. Initially, 1 mL of purified water was added to 0.5 g of Calcium Chloride (available from Tomida Pharmaceutical Co., Ltd, Japan). To this mixture, there were added 30 g of Concentrated Glycerine (available from Nippon Oil and Fats Co., Ltd., Japan) and 20 g of Propylene Glycol (available from Wako Junyaku Kogyo Kabushiki Kaisha, Japan). Further, 1.0 g of a proteolytic enzyme derived from Bacillus ("Alkaline Protease GL-440 available from Kyowa-Solzyme K. K., Japan) and 1.0 g of Sodium Borate as the buffer (available from Tomida Pharmaceutical Co., Ltd, Japan ) were dissolved in the mixture. To the thus obtained solution, there was added purified water so that the solution had a total volume of 100 mL. Then, the solution was adjusted of its pH value to 6.0 with 1.0N hydrochloric acid, whereby the specimen No. 1 of the present cleaning solution was obtained.

In the same manner as the specimen No. 1, specimens Nos. 2–6 of the present cleaning solution were prepared so as to have the respective compositions as also indicated in TABLE 1. Unlike the specimen No. 1, the specimens Nos. 2, 3, 4 and 6 further include the nonionic surface active agent (polyoxyethylene-polyoxypropylene block copolymer). Described more specifically, the specimens Nos. 2, 4 and 6 of the contact lens cleaning solution include the nonionic surface active agent, i.e., "Pluronic L-64" (available from ASAHI DENKA KOGYO K. K., Japan), in the respective amounts of 2 g, 1 g and 1.5 g, while the specimen No. 3 includes the nonionic surface active agent, i.e., "Lutrol F-127" (available from BASF) in an amount of 1 g. The specimens Nos. 2, 5 and 6 of the cleaning solution include, as the proteolytic enzyme, 1.2 g of "SP-614" (available from Novo Industry Japan). In the specimens Nos. 4 and 6, 2.5N aqueous solution of sodium hydroxide is used in place of 1.0N hydrochloric acid which was used in the specimen No. 1. As compared with the specimens Nos. 1–3 of the cleaning solution, the amount of glycerine included in the cleaning solution specimen No. 4 is increased to 50 g, while the amount of propylene glycol included in the cleaning solution specimen No. 5 is increased to 50 g. In the cleaning solution specimen No. 6, the amounts of glycerine and propylene glycol are both increased to 40 g.

TABLE 1

| | Present invention | | | | | |
|---|---|---|---|---|---|---|
| | 1 | 2 | 3 | 4 | 5 | 6 |
| proteolytic enzyme (GL-440) | 1.0 | — | 1.0 | 1.0 | — | — |
| proteolytic enzyme (SP-614) | — | 1.2 | — | — | 1.2 | 1.2 |
| propylene glycol | 20 | 20 | 30 | 20 | 50 | 40 |
| glycerine | 30 | 30 | 20 | 50 | 15 | 40 |
| calcium chloride dihydrates | 0.5 | 0.05 | 0.5 | 0.2 | 0.5 | 0.5 |
| buffer (sodium borate) | 1.0 | 1.0 | 1.0 | 1.2 | 1.0 | 1.5 |
| 1.0N hydrochloric acid | | * | | — | * | — |
| 2.5N aqueous solution of sodium hydroxide | — | — | — | * | — | * |
| nonionic surface active agent (Pluronic L-64) | — | 2.0 | — | 1.0 | — | 1.5 |
| nonionic surface active agent (Lutrol F127) | — | — | 1.0 | — | — | — |
| purified water | balance | | | | | |
| pH | 6.0 | | | | | |

(unit: g)
*: as needed

As comparative examples, there were prepared specimens Nos. 1–6 of the cleaning solution in the same manner as the specimen No. 1 of the cleaning solution according to the present invention, so that the specimens Nos. 1–6 of the comparative examples have the respective compositions as indicated in TABLE 2. The specimens Nos. 1–3 according to the comparative examples do not include the surface active agent. The cleaning solution specimens Nos. 4 and 5 of the comparative examples respectively include 1.0 g of cationic surface active agent, i.e., "CATION PB300" (available from Nippon Oil and Fats Co., Ltd., Japan) and 1.0 g of anionic surface active agent, i.e., "Nikkol OS-14" (available from NIKKO CHEMICALS CO., LTD., Japan), while the specimen No. 6 includes 1.0 g of amphoteric surface active agent, i.e., "NISSAN ANON LG" (available from Nippon Oil and Fats Co., Ltd., Japan).

TABLE 2

| | Comparative examples | | | | | |
|---|---|---|---|---|---|---|
| | 1 | 2 | 3 | 4 | 5 | 6 |
| proteolytic enzyme (GL-440) | 1.0 | 1.0 | 1.0 | 1.0 | 1.0 | 1.0 |
| propylene glycol | — | 10 | 40 | 20 | 20 | 20 |
| glycerine | 50 | 20 | — | 30 | 30 | 30 |
| calcium chloride dihydrates | 0.5 | 0.5 | 0.5 | 0.5 | 0.5 | 0.5 |
| buffer (sodium borate) 1.0N hydrochloric acid | 1.0 | 1.0 | 1.0 as needed | 1.0 | 1.0 | 1.0 |
| cationic surface active agent (CATION PB300) | — | — | — | 1.0 | — | — |
| anionic surface active agent (Nikkol OS-14) | — | — | — | — | 1.0 | — |
| amphoteric surface active agent (NISSAN ANON LG) | — | — | — | — | — | 1.0 |
| purified water | balance | | | | | |
| pH | 6.0 | | | | | |

(unit: g)

<Enzyme stability test>

For each of the specimens Nos. 1–6 of the cleaning solution according to the present invention and the specimen No. 3 of the cleaning solution according to the comparative examples, there were measured, in the following manner, the enzyme activity upon preparation of each specimen of the cleaning solution, and the enzyme activity after each specimen was stored at the temperature of 60° C. for one week.

Initially, each specimen of the cleaning solution was diluted with purified water at a suitable dilution ratio "d". To 1 mL of each diluted specimen of the cleaning solution, protein in the form of 0.6 w/v % aqueous solution of casein (pH 7.00, 0.05M sodium monohydrogenphosphate) was added in an amount of 5 mL while it was kept at 37° C. The thus obtained mixture was kept at 37° C. for 10 minutes, so that the protein was processed by the proteolytic enzyme included in each specimen of the cleaning solution. Subsequently, 5 mL of precipitant (i.e., a mixed solution consisting of 0.11M trichloroacetic acid, 0.22M sodium acetate and 0.33M acetic acid) was added to the above mixture, whereby undecomposed protein was precipitated. Then, the mixture was subjected to filtration, and the filtrate was measured of its absorbance (A) at 275 nm. As control experiments, each specimen of the cleaning solution was diluted with purified water at the dilution ratio "d". To 1 mL of each diluted specimen of the cleaning solution, 5 mL of the above-described precipitant was added. Further, 5 mL of the above-described aqueous solution of casein was added, so that the protein was precipitated. The mixture was subjected to filtration, and the filtrate was measured of its absorbance ($A_O$) at 275 nm. The activity of the proteolytic enzyme was calculated from the following equation (1) based on the results of measurement. The activity of the proteolytic enzyme is defined as $1\mu$ when the enzyme activity is capable of producing, for one minute, non-protein material that provides absorbance corresponding to an amount of $1\times10^6$ of tyrosine at 275 nm.

Proteolytic enzyme activity (u/mL) = $\{(A - A_O)/(A_s)\} \times 50 \times 11 \times d/10$ (1)

wherein $A_S$: absorbance per 50 $\mu$g/mL of tyrosine at 275 nm=391 d: dilution ratio

The residual activity of the proteolytic enzyme was calculated from the following equation (2), on the basis of the enzyme activity measured upon preparation of each specimen of the cleaning solution and the enzyme activity measured after each specimen of the cleaning solution was stored at 60° C. for one week, according to the above equation (1). The results of calculation are indicated in TABLE 3.

Residual activity (%) = (2)

{(the proteolytic enzyme activity after storage at 60° C. for one week)/

(the proteolytic enzyme activity upon preparation)} × 100

TABLE 3

| specimen No. | enzyme activity upon preparation | enzyme activity after one week | residual enzyme activity (%) |
|---|---|---|---|
| Present Invention | | | |
| 1 | 2133 | 2048 | 96 |
| 2 | 2284 | 2325 | 102 |
| 3 | 1841 | 1593 | 87 |
| 4 | 2328 | 2287 | 98 |
| 5 | 2221 | 2178 | 98 |
| 6 | 2517 | 1922 | 76 |
| 3* | 2115 | 54 | 3 |

*: comparative example

It was confirmed from the results of TABLE 3 that the cleaning solution according to the present invention exhibited excellent enzyme stability. In contrast, it was recognized that the cleaning solution according to the comparative examples did not exhibit sufficient enzyme stability.

Example 2

The contact lens cleaning solution according to the present invention was inspected of its inhibitory effect on development of bacteria in order to confirm the disinfecting effect exhibited by the cleaning solution.

Initially, 40.0 g of Tryptone Soya Agar (available from EIKEN CHEMICAL CO., LTD., Japan) was dissolved in 1000 mL of distilled water. This mixture was subjected to steam sterilization under pressure at 121° C. for 20 minutes, whereby Tryptone Soya agar medium was prepared.

Next, 0.13 mL of the specimens Nos. 1–3 of the cleaning solution according to the present invention and 0.13 mL of the specimen No. 5 of the cleaning solution according to the comparative examples were diluted in the respective test tubes with 10 mL of the commercially available contact lens disinfecting liquid (i.e., ReNu Multi-Purpose Solution available from BAUSCH & LOMB INCORPORATED, U.S.A.) which contains polyhexamethylene biguanide as the ionic antimicrobial agent. To each of the test tubes, there was added 0.05 mL of bacteria liquid which contains either Serratia marcescens or Staphylococcus aureus, in an amount of $10_8$cfu/mL–$10^9$cfu/mL. Each of the mixtures was stirred, and adjusted so as to contain one of the Serratia marcescens or Staphylococcus aureus in an amount of $10^6$cfu/mL–$10^7$cfu/mL. The mixture was left at room temperature for 4 hours. (Hereinafter, the mixture is referred to as "bacteria suspension".) Then, 1 mL of the bacteria suspension was taken out of each test tube, and diluted every ten times with physiological salt solution, whereby samples of each bacteria suspension were obtained. Each of the thus obtained samples was cultured by using 17 mL of Tryptone Soya agar medium, and was measured of its viable cell count per 1 mL by plate dilution method. On the basis of the obtained value, the viable cell count per 1 mL of each bacteria suspension was calculated. The viable cell count was measured by the plate dilution method, using the samples wherein colonies were suitably dispersed on the plate after culture, and the development of the bacteria was not inhibited. The results of the measurement are indicated in TABLE 4. TABLE 4 also shows the result of the measurement in a control experiment, wherein only the commercially available contact lens disinfecting liquid was used.

TABLE 4

| Specimen No. | bacteria | |
|---|---|---|
| | Serratia marcescens | Staphylococcus aureus |
| control experiment Present Invention | $10^2$ | $10^2$ |
| 1 | $10^2$ | $10^2$ |
| 2 | $10^2$ | $10^2$ |
| 3 | $10^2$ | $10^2$ |
| 5* | $10^5$ | $10^4$ |

*: comparative example

It will be apparent from the results of TABLE 4 that the contact lens cleaning solution according to the present invention exhibited excellent disinfecting effect.

Example 3

The cleaning solution was inspected of its disinfecting effect with respect to Serratia marcescens and Staphylococcus aureus in the same manner as in Example 2. Described more specifically, as the diluting liquid or diluent, there were used two kinds of commercially available contact lens disinfecting liquid, i.e., "ReNu Multi-Purpose Solution" (available from BAUSCH & LOMB INCORPORATED, U.S.A.) which contains polyhexamethylene biguanide as the ionic antimicrobial agent, and "OPTI-FREE" (available from Alcon Laboratories Incorporated, U.S.A.) which contains, as the ionic antimicrobial agent, α-4-[tris(2-hydroxyethyl)ammonium-2-butenyl]poly[1-dimethylammonium-2-butenyl]-ω-tris(2-hydroxyethyl) ammonium chloride. As the contact lens cleaning solution, there were prepared the specimen No. 1 of the cleaning solution of the present invention, specimen NO. 5 of the cleaning solution according to the comparative examples and two kinds of commercially available enzyme cleaning agent in tablet form, i.e., "ReNu Effervescent Enzymatic Cleaner" (available from BAUSCH & LOMB INCORPORATED, U.S.A.) and "OPTI-FREE ENZYMATIC CLEANER" (available from Alcon Laboratories Incorporated, U.S.A.). Each of the diluting liquids and each of the cleaning solutions were combined as indicated in TABLE 5. The results of the measurement are indicated also in TABLE 5.

As is apparent from the results of TABLE 5, the contact lens cleaning solution (the specimen No. 1) of the present invention exhibited excellent disinfecting effect as compared with the cleaning solution specimen No. 5 according to the comparative examples and the commercially available proteolytic cleaning agents. It was recognized that the anionic surface active agent included in the specimen No. 5 of the cleaning solution according to the comparative examples deteriorated the disinfecting effect exhibited by the disinfecting liquid used for diluting the cleaning solution. It was further recognized that the proteolytic agents in tablet form such as the ReNu Effervescent Enzymatic Cleaner and OPTI-FREE ENZYMATIC CLEANER also deteriorated the disinfecting effect.

TABLE 5

| Diluent | Cleaning solution or agent | Staphylococcus aureus | Serratia marcescens |
|---|---|---|---|
| | START | $10^6$ | $10^6$ |
| ReNu Multi-Purpose Solution | — | $10^3$ | $10^2$ |
| ReNu Multi-Purpose Solution | ReNu Effervescent Enzymatic Cleaner | $10^5$ | $10^5$ |
| ReNu Multi-Purpose Solution | Specimen No. 1 of the present invention | $10^3$ | $10^2$ |
| ReNu Multi-Purpose Solution | Specimen No. 5 of the comparative examples | $10^5$ | $10^5$ |
| OPTI-FREE | — | $10^2$ | $10^3$ |
| OPTI-FREE | OPTI-FREE ENZYMATIC CLEANER | $10^4$ | $10^3$ |
| OPTI-FREE | Specimen No. 1 of the present invention | $10^3$ | $10^2$ |
| OPTI-FREE | Specimen No. 5 of the comparative examples | $10^5$ | $10^5$ |

Example 4

One droplet of each of the specimens Nos. 1–3 of the cleaning solution of the present invention and the specimens Nos. 4 and 6 of the cleaning solution according to the comparative examples was added to 2 mL of the commercially available cleaning and storing liquid for the hard contact lens ("O$_2$ CARE" available from Menicon Co., Ltd), whereby five mixtures corresponding to the specimens Nos. 1–3 of the present invetnion and the specimens Nos. 4 and 6 accoring to the comparative examples were obtained. It was observed that the mixtures corresponding to the specimens Nos. 4 and 6 according to the comparative examples turned white, while the mixtures corresponding to the specimens Nos. 1–3 of the present invention did not turn white.

Thus, it was confirmed that the contact lens cleaning solution of the present invention gave no adverse influence on the contact lens cleaning and storing liquid for the hard contact lens when the cleaning solution was diluted with the liquid. On the other hand, it was found that the cleaning and storing liquid for the hard contact lens turned white by addition of the cleaning solution which included the cationic or amphoteric surface active agent. Accordingly, it was revealed that the cleaning solution including the cationic or amphoteric surface active agent cannot be used in combination with the commercially available cleaning and storing liquid for the hard contact lens.

Example 5

In this Example 5, the cleaning solution was examined of its preservative effect in the following manner. Initially, there were prepared two kinds of culture media, i.e., Glucose Peptone agar medium and Tryptone Soya agar medium. The former was obtained by dissolving, in 10000 mL of distilled water, 28.5 g of commercially available Glucose Peptone Agar for the sterility test (available from EIKEN CHEMICAL CO., LTD., Japan) and 15 g of agar powder for bacteria medium (available from Wako Junyaku Kogyo Kabushiki Kaisha, Japan), and steam-sterilizing the mixture at 121° C. for 20 minutes. The latter was obtained by dissolving, in 10000 mL of distilled water, 40.0 g of commercially available Tryptone Soya Agar (available from EIKEN CHEMICAL CO., LTD., Japan), and steam-sterilizing the mixture at 121° C. for 20 minutes.

10 mL of the specimen No. 1 of the contact lens cleaning solution according to the present invention was poured into a plurality of test tubes. Next, there were prepared bacteria or fungi liquid which respectively contain *Aspergillus niger, Candida albicans, Staphylococcus aureus, Pseudomonas cepacia* and *Escherichia coli*, in an amount of $10^8$cfu/mL–$10^9$cfu/mL. The thus prepared bacteria or fungi liquids were respectively added to the test tubes of the cleaning solution specimen No. 1, in an amount of of 0.01 mL. The mixtures were stirred so as to provide various kinds of bacteria or fungi suspensions each including any one of the above-described bacteria and fungi in an amount of $10^6$cfu/mL–$10^7$cfu/mL. The thus obtained bacteria or fungi suspensions were kept at room temperature for 28 days. After 14 days and after 28 days, 1 mL of the bacteria or fungi suspensions were taken out of each of the test tubes, and diluted every ten times with physiological salt solution, whereby samples of the bacteria or fungi suspensions after 14 days and after 28 days were respectively provided. The viable cell count per 1 mL of each sample were measured by the plate dilution method. More specifically described, the viable cell counts of the samples of the fungi suspensions of *Aspergillus niger* and *Candida albicans* were measured by using 20 mL of the Glucose Peptone agar medium, while those of the samples of the bacteria suspensions of *Staphylococcus aureus, Pseudomonas cepacia* and *Escherichia coli* were measured by using 17 mL of the Tryptone Soya agar medium. On the basis of the obtained values, the viable cell count per 1 mL of each of the bacteria or fungi suspensions was calculated. The results are indicated in TABLE 6. In the plate dilution method, the samples having the concentrations which do not inhibit the development of the bacteria or fungi were employed.

TABLE 6

|  | START | after 14 days | after 28 days |
|---|---|---|---|
| *Aspergillus niger* | $10^5$ | $10^4$ | $10^2$ |
| *Candida albicans* | $10^5$ | below $10^2$ | 0 |
| *Staphylococcus aureus* | $10^6$ | 0 | 0 |
| *Pseudomonas cepacia* | $10^6$ | 0 | 0 |
| *Escherichia coli* | $10^6$ | $10^3$ | 0 |

The specimens Nos. 2 and 3 of the cleaning solution of the present invention and the specimens Nos. 1 and 2 of the cleaning solution according to the comparative examples were inspected of the preservative effect with respect to *Candida albicans* and *Staphylococcus aureus*, in the same manner as in Example 5. The viable cell counts after 14 days were similarly measured, and the results of measurement are indicated in TABLE 7.

TABLE 7

|  | Cleaning solution | | | |
|---|---|---|---|---|
|  | Specimen No. 2* | Specimen No. 3* | Specimen No. 1** | Specimen No. 2** |
| *Candida albicans* | below 10 | below 10 | $10^5$ | $10^5$ |
| *Staphylococcus aureus* | below 10 | below 10 | below 10 | below 10 |

*: according to the present invention
**: according to the comparative examples

It will be understood from the results of TABLES 6 and 7 that the contact lens cleaning solution employed in the present invention exhibited a high degree of preservative effect. The results also show that the cleaning solution exhibited insufficient preservative effect when the amount of propylene glycol included in the cleaning solution is relatively small.

Example 6

Initially, there was prepared a protein-contaminated liquid in the form of artificial tear fluid (pH 7.4), which includes: 0.388 g of albumin; 0.161 g of γ-globulin; 0.120 g of lysozyme; 0.900 g of sodium chloride; 0.015 g of calcium chloride (dihydrates); 0.104 g of sodium dihydrogenphosphate(dihydrates); 5 mL of 1N aqueous solution of sodium hydroxide; and 100 mL of purified water. Among these reagents, the γ-globulin is available from SIGMA, while the others are available from Wako Junyaku Kogyo Kabushiki Kaisha.

Next, five hard contact lenses with high oxygen permeability ("MENICON SUPER EX" available from Menicon Co., Ltd, Japan) were prepared. These contact lenses were boiled in 1.5 mL of the artificial tear fluid prepared as described above for 30 minutes, and kept in cool water for 30 minutes. Subsequently, each of the contact lenses were observed of its surfaces by a dark-field microscope of 20× magnification. It was confirmed that the entire surfaces of all of the contact lenses were soiled with white protein stains.

One droplet of each of the specimens Nos. 1–3 of the cleaning solution according to the present invention was added to 2 mL of the commercially available contact lens cleaning agent ("Total" available from Allergan, Inc., U.S.A.) which contains benzalkonium chloride as the ionic antimicrobial agent, whereby three treatment liquids corresponding to the specimens Nos. 1–3 were obtained. The contact lenses soiled with the protein stains were soaked in the respective treatment liquids for 2 hours. Thereafter, these contact lenses were observed by the dark-field microscope of 20× magnification, and it was confirmed that the protein stains were completely removed from the contact lens surfaces.

Another contact lens soiled with the protein stains as described above was soaked in the commercially available cleaning agent as described above ("Total" available from Allergan, Inc., U.S.A.). Then, the contact lens was cleaned by finger rubbing. It was confirmed that the white protein stains adhering to the entire surfaces of the contact lens remained without being completely removed from the lens surfaces.

It will be understood from the above description that the method of cleaning and disinfecting the contact lens of the present invention assures excellent cleaning effect by using the contact lens cleaning solution having the specific composition according to the present invention. That is, the cleaning solution of the present invention does not adversely influence the disinfecting effect of the contact lens disinfecting or storing liquid with which the cleaning solution is diluted, whereby the contact lens can be cleaned and disinfected simultaneously with high efficiency according to the method of the present invention.

What is claimed is:

1. A method of simultaneously cleaning and disinfecting a contact lens comprising the steps of:

preparing a cleaning solution for said contact lens comprising a protein stain removing effective amount of a proteolytic enzyme, 20–40 w/v % (percent by weight/volume) of propylene glycol, 20–40 w/v % of glycerine, and water, the total content of said propylene glycol and said glycerine being in a range of 40–60 w/v %;

diluting said cleaning solution with a disinfecting or storing liquid for said contact lens that contains an ionic antimicrobial agent, so as to provide a diluted solution; and immersing said contact lens in said diluted solution.

2. A method according to claim 1, wherein said effective amount of said proteolytic enzyme is in a range of 0.1–10 w/v %.

3. A method according to claim 2, wherein said effective amount of said proteolytic enzyme is in a range of 0.5–5 w/v %.

4. A method according to claim 1, wherein said cleaning solution further comprises a nonionic surface active agent in an amount up to 10 w/v %.

5. A method according to claim 4, wherein said nonionic surface active agent is included in said cleaning solution in an amount of 0.1–3 w/v %.

6. A method according to claim 4, wherein said nonionic surface active agent is selected from the group consisting of polyoxyethylene-polyoxypropylene block copolymer, condensation product of polyoxyethylene and ethylenediamine, fatty acid glyceryl ester, alkanoic acid sucrose ester, polyoxyethylene alkylamine, sorbitan fatty acid polyoxyethylene ester, fatty acid triethanolamine ester, polyoxyethylene alkyl ether, polyoxyethylene alkylphenyl ether and polyoxyethylene polystyrylphenyl ether.

7. A method according to claim 1, wherein said proteolytic enzyme included in said cleaning solution is serine protease, and calcium ion is further included in said cleaning solution in a concentration of 0.5–250 mM/l.

8. A method according to claim 7, wherein said calcium ion is further included in said cleaning solution in a concentration of 3–30 mM/l.

9. A method according to claim 7, wherein said calcium ion is provided in the form of a calcium salt.

10. A method according to claim 9, wherein said calcium salt is selected from the group consisting of calcium chloride, calcium sulfate and calcium acetate.

11. A method according to claim 1, wherein said ionic antimicrobial agent is selected from the group consisting of biguanides, quaternary ammonium salts, sorbic acid, benzoic acid and salts thereof.

12. A method according to claim 1, wherein pH of said cleaning solution is held in a range of 5.0–9.5.

13. A method according to claim 12, wherein pH of said cleaning solution is held in a range of 5.5–7.5.

14. A method according to claim 1, wherein a buffer agent is included in said cleaning solution in an amount of 0.1–10 w/v %.

15. A method according to claim 1, wherein said dilution has a pH range of 6.0–8.0 and an osmotic pressure value in a range of 200–600 mOsm.

16. A method according to claim 15, wherein said dilution has a pH value in a range of 6.5–7.5 and an osmotic pressure value in a range of 300–450 mOsm.

17. A method according to claim 14, wherein said buffer agent comprises a combination of tris(hydroxymethyl) aminomethane and hydrochloric acid.

18. A method according to claim 14, wherein said buffer agent comprises one of boric acid, borax and mixtures thereof.

* * * * *